United States Patent [19]

Aitken

[11] Patent Number: 4,671,296
[45] Date of Patent: Jun. 9, 1987

[54] RACEHORSE ATHLETIC CONDITION MEASURING INSTRUMENT

[76] Inventor: Louis F. Aitken, 12 St. Andrew Dr., Clayton, Mo. 63124

[21] Appl. No.: 686,758

[22] Filed: Dec. 27, 1984

[51] Int. Cl.⁴ ............................ A61B 5/02; G01K 7/12
[52] U.S. Cl. ..................................... 128/671; 128/716; 128/721; 128/736; 374/143
[58] Field of Search ............... 374/163, 141, 142, 143; 128/674, 675, 680, 681, 687, 716, 724, 736, 689, 690, 14, 19, 721, 714, 748, 671

[56] References Cited

U.S. PATENT DOCUMENTS

| | | | |
|---|---|---|---|
| 3,605,495 | 9/1971 | Krause et al. | 374/143 |
| 3,610,208 | 10/1971 | Penning | 374/143 X |
| 3,766,908 | 10/1973 | Haynes | 374/142 |
| 3,916,877 | 11/1975 | Beckman | 374/142 |
| 3,999,537 | 12/1976 | Noiles | 374/142 |
| 4,006,735 | 2/1977 | Hittman et al. | 73/715 X |
| 4,028,943 | 6/1977 | Hyanova et al. | 374/143 |
| 4,036,211 | 7/1977 | Veth et al. | 128/724 |
| 4,195,349 | 3/1980 | Balkanli | 374/143 |
| 4,202,353 | 5/1980 | Hirsch et al. | 128/724 |
| 4,270,547 | 6/1981 | Steffen et al. | 128/738 |
| 4,366,714 | 1/1983 | Adorni | 374/143 |
| 4,483,564 | 1/1985 | Epstein | 128/687 |
| 4,510,941 | 4/1985 | Semrow et al. | 128/736 X |
| 4,563,902 | 1/1986 | Kohnlechner | 374/143 X |
| 4,577,510 | 3/1986 | Bur et al. | 374/143 X |

Primary Examiner—Daniel M. Yasich
Attorney, Agent, or Firm—Lane and Aitken

[57] ABSTRACT

In an instrument designed to provide a quantitative measurement of the athletic condition of racehorses, a pressure sensitive transducer is mounted on a rectal probe, which is of a size and shape to be inserted into the rectal cavity of a racehorse. Circuitry is provided to separate the components in the signal produced by the transducer caused by respiration and caused by the cardiovascular pulse. The cardiovascular pulse rate and the respiration rate are calculated from these two components and displayed on a console connected to the probe. The instrument is also provided with a thermocouple on the rectal probe, which is connected in a conventional electronic thermometer circuit, which controls a display on the console of the instrument to provide an indication of the temperature of the racehorse.

9 Claims, 2 Drawing Figures

RACEHORSE ATHLETIC CONDITION MEASURING INSTRUMENT

This invention relates to an instrument for providing a rapid indication of the athletic condition of racehorses and more particularly to an instrument, which provides this information by means of a rectal probe.

In the sport of horse racing, particularly in thoroughbred racing, the art of conditioning racehorses so as to bring a racehorse into peak condition at the time of a race is difficult and involves much guesswork on the part of the trainer. Yet the success of an individual racehorse in a given race depends upon the trainer being able to achieve this peak of conditioning at the time of the race. One of the difficulties in the training methods, as presently practiced, is that there is presently no convenient way to precisely measure the condition of a racehorse. Present methods involve keeping track of the workout times of the racehorse in training and subjectively appraising the racehorse on the completion of each workout. These methods all involve substantial subjective judgement and guesswork by the trainer and accordingly, the trainer is never really quite as sure of the condition of a given racehorse as he could be.

The present invention provides an instrument, which provides a convenient method of providing a more quantitative measure of the condition of the racehorse. In accordance with the present invention, a rectal probe is provided, which will simultaneously measure the racehorse's temperature respiration rate, and cardiovascular pulse rate. In athletes, both human and animal, the temperature, respiration rate and pulse rate will increase to well above normal rest levels during and immediately after an athletic workout. The athletic condition of the athlete can be accurately judged by how long it takes these measurements to return to their normal rest levels, or alternatively how much they have returned toward their rest level, a short time interval after an athletic workout. In addition, the temperature measurement will provide an indication of whether or not the athlete has an infection, which is affecting the other two measurements.

The present invention provides a rectal probe to enable the trainer to make all three measurements, temperature, respiration, and pulse conveniently and quickly and thus, obtain an accurate indication of the condition of the racehorse. The rectal probe is provided with a conventional electronic thermometer, and with a pressure transducer, which will sense variations in pressure in the rectal cavity. As the horse breathes, the pressure in the rectal cavity sensed by the transducer will go up and down with the respiration cycle. In addition, the pressure in the rectal cavity will vary with the animal's cardiovascular pulse. The variation in the pressure with the respiration will be at the relatively low frequency of the horse's respiration rate, whereas the variation in pressure with the cardiovascular pulse will be at a much higher frequency. By means of filters, the pressure variations due to the respiration and the cardiovascular pulse rate are separated and the respiration rate and the cardiovascular pulse rate are computed from these pressure variations and are displayed on a console connected to the probe. In addition, the temperature measured by the electronic thermometer is also displayed on the console.

To make use of this condition measuring instrument, the trainer will insert the probe into the rectal cavity of the horse immediately following a workout and note the temperature, respiration and pulse measurements. A short time later, e.g. twenty minutes later, the trainer will take the measurements again and note the differences. The differences noted, particularly of the respiration and pulse rates, will provide a reliable indication of the present condition of the racehorse.

Accordingly, an object of the present invention is to provide an improved instrument for measuring the athletic condition of a horse.

A further object of the present invention is to provide an instrument by which the pulse rate and respiration rate of an animal, such as a racehorse, can be obtained quickly and easily.

A further object of the present invention is to provide an instrument, which will provide an indication of the pulse rate of a horse from the pressure variations in the rectal cavity.

A further object of the present invention is to provide an instrument, which will provide a measurement of the respiration rate of a horse from the pressure variations in the rectal cavity.

Further objects and advantages of the present invention will become readily apparent as the following detailed description of the invention unfolds and when taken in conjunction with the drawings.

DESCRIPTION OF A PREFERRED EMBODIMENT

Figure 1:
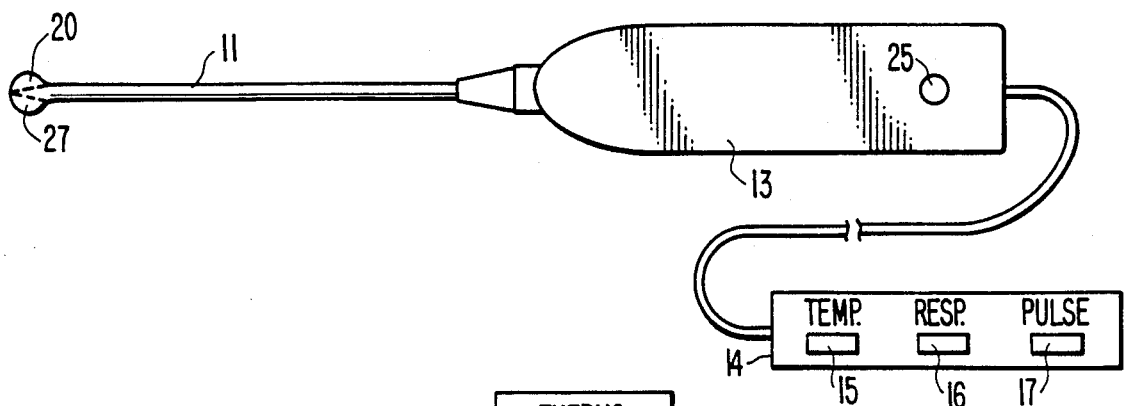
FIG. 1 illustrates the instrument of the present invention.

As shown in FIG. 1, the instrument comprises a probe 11 of a size and shape to be inserted into the rectal cavity of a racehorse. The rectal probe contains, near its tip, a thermocouple 20 to sense the temperature in the rectal cavity and a pressure sensitive transducer 27. The probe includes a handle 13, which is provided with a push button 25 to initiate a measurement operation. An electric cable connects the probe 11 to a console 19 and transmits signals from the thermocouple 20, the pressure sensitive transducer 27, and from a switch operated by the push button 25 to circuitry in the console. The console is provided with three liquid crystal readout displays 15, 16 and 17, providing a digital readout indication of the temperature sensed by thermocouple 20 and the respiration rate and the pulse sensed by the pressure sensitive transducer 27.

Figure 2:
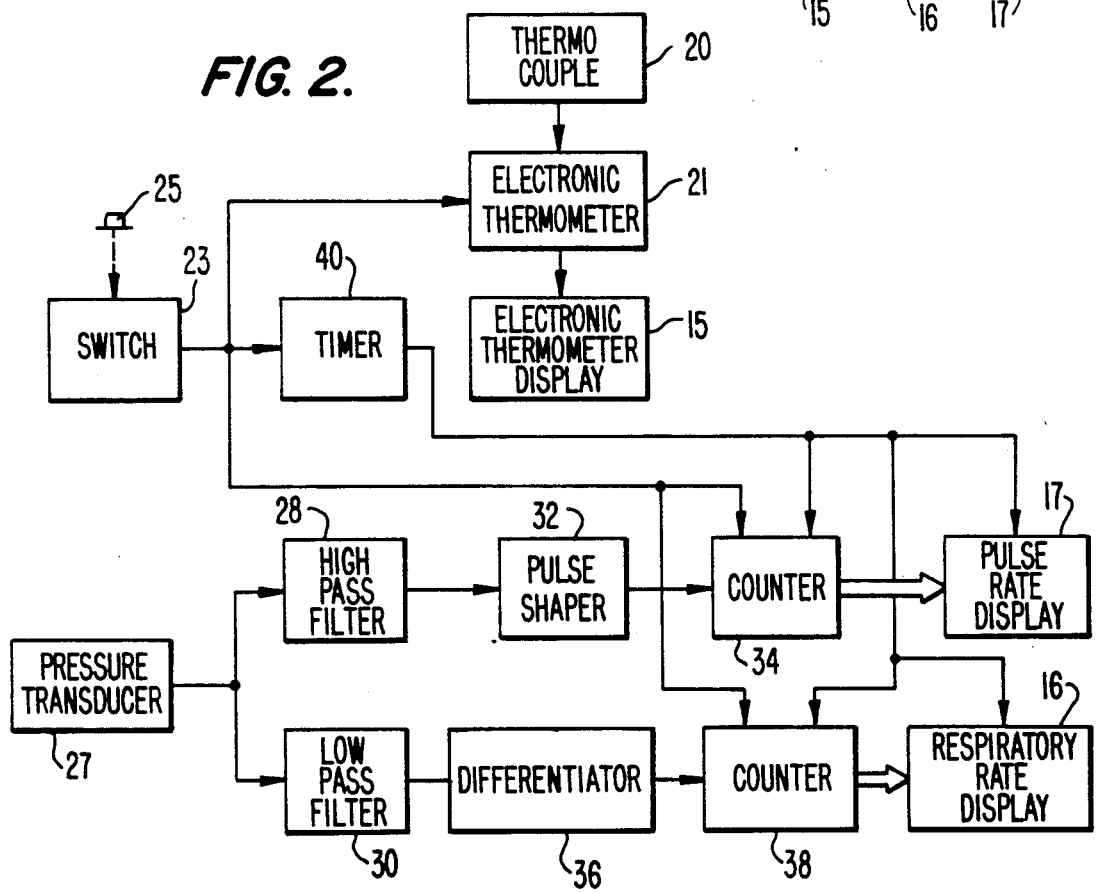
FIG. 2 is a block diagram of the circuitry employed in the instrument of the present invention.

As shown in FIG. 2, the thermocouple 20 is part of a conventional thermometer circuit 21, which is activated by the momentary closure of the switch 23. The switch 23 is actuated by the push button 25 mounted on the handle 13.

To use the instrument, the trainer will insert the probe 11 into the rectal cavity and then actuate the push button 25 to momentarily close the switch 23. This will initiate the electronic thermometer circuit 21 to respond to the signal from the thermocouple and control the electronic thermometer display digitally display the temperature sensed by the thermocouple. The pressure transducer 27, will produce an electrical signal varying in accordance with the variation in pressure in the rectal cavity. This electrical signal applied to a high pass filter 28 and a low pass filter 30. The high pass filter is set to pass the signals caused by the variation in pressure due to the horse's cardiovascular pulse and filter out the variations resulting from the horses respiration. For example, the high pass filter might be set to only pass signals which are above 200 hertz. While the horses pulse rate may be considerably below 200 hertz, the pulses in the wave form representing the cardiovascular pulse will have considerably higher frequency components and accordingly will be readily passed by the high pass filter 28. These pulses are applied to a pulse shaper 32, where they are shaped and then applied to a counter 34. The low pass filter 30 is set to pass the component of the pressure transducer signal caused by pressure variations in the rectal cavity due to respiration and filter out the component of the signal caused by the cardiovascular pulse. The filter 30 may be set to pass signals below 150 hertz and filter out signals above 150 hertz. The resulting output signals from the filter 30 may have a low amplitude component caused by the cardiovascular pulse, but such a component will be of such low amplitude compared with the component due to the pressure variation caused by respiration that it can be disregarded. The output from the low pass filter 30 thus will be a rising and falling signal varying in accordance with the horses respiration. This signal is applied to a differentiator 36, which will produce a pulse each time the applied signal from the low pass filter changes direction. Thus, the differentiator 36 will produce two pulses for each cycle of respiration by the horse. The pulses produced by the differentiator 36 are applied to a counter 38.

When the switch 23 is momentarily closed by actuation of the button 25, it resets the counters 34 and 38 to 0, whereupon they begin counting the pulses applied from the pulse shaper 32 and the differentiator 36 respectively. The momentary closure of the switch 23 also actuates a timer 40, which will time out after a time period of 60 seconds. When the timer 40 times out, it applies a signal to the counters 34 and 38 to disable these counters 34 and 38 from counting further. As a result, the count in the counter 34 will represent the cardiovascular pulse rate of the horse over the last 60 seconds and the count in the counter 38 will represent the respiratory rate of the horse over the last 60 seconds. The timer 40 also applies a signal to the respiratory rate display 16 and the pulse rate display 17 to cause these displays to digitally display the counts in the counters 34 and 38 and thus, display the horse's respiratory rate and the pulse rate.

As indicated above, to use the instrument of the present invention, the trainer will insert the probe into the rectal cavity immediately after a horse's workout and obtain the temperature, cardiovascular pulse rate and respiratory rate measurements. Then after a delay of a short period of time, cush as twenty minutes, the trainer will take a second measurement of these same physiological parameters. By comparing the two readings, the trainer obtains a indication of the physical condition of the horse.

In the preferred embodiment of the instrument of the present invention, the measurements of the temperature, respiratory rate and cardiovascular pulse rate are all taken. However, it is contemplated that the instrument could omit measurement of at least one of the three parameters, or perhaps both the temperature and either one of the measurements of the respiration or pulse rate and the probe would still be a valuable tool to provide a rapid indication of the athletic condition of the horse. The time interval of 60 seconds over which the respiration and pulse rate measurements are taken has been chosen to reduce the calculation steps required in the instrument. The measurement interval could be shortened to reduce the time required to make the measurement or lengthened to increase the precision of the measurement. These and many other modifications may be made to the instrument of the present invention without departing from the spirit and scope of the invention, which is defined in the appended claims.

What is claimed is:

1. An instrument for quantitatively determining the athletic condition of a horse comprising a probe sized and shaped to be inserted into the rectal cavity of a horse, pressure sensing means mounted on said probe, connected in an electrical circuit and operable to sense pressure variations in a rectal cavity of a horse when said probe is inserted in such rectal cavity, and means in said electrical circuit responsive to the pressure variations sensed by said pressure sensing means to selectively indicate the cardiovascular pulse rate of the horse.

2. An instrument, as recited in claim 1, further comprising means responsive to the pressure variations sensed by said pressure sensing means when said probe is inserted in the rectal cavity of a horse, to indicate the respiration rate of the horse.

3. An instrument, as recited in claim 2, further comprising temperature sensing means mounted on said probe and, operable to sense the temperature within the rectal cavity in which said probe is inserted, and means to indicate the temperature sensed by said temperature sensing meals.

4. An instrument, as recited in claim 1 further comprising temperature sensing means on said rectal probe to sense the temperature within the rectal cavity in which said probe is inserted, and means to indicate the temperature sensed by said temperature sensing means.

5. An instrument for quantitatively determining the athletic condition of a horse comprising a probe sized and shaped to be inserted into the rectal cavity of a horse, pressure sensing means mounted on said probe connected in an electrical circuit and operable to sense the pressure variations in the rectal cavity of a horse when said probe is inserted to such rectal cavity, and means in said electrical circuit responsive to the pressure variations sensed by said pressure sensing means to indicate selectively the respiratory rate of the horse.

6. An instrument, as recited in claim 5, further comprising temperature sensing means mounted on said probe to sense the temperature within the rectal cavity of the horse in which said probe is inserted, and means responsive to the temperature sensed by said temperature sensing means to indicate the temperature in the rectal cavity of the horse.

7. A method of quantitatively determining the athletic condition of a horse comprising inserting a pressure sensitive transducer which is connected to an electrical indicating unit into the rectal cavity of the horse and selectively deriving the cardiovascular pulse rate of the horse from the pressure variations sensed by the pressure transducer.

8. A method as recited in claim 7, further comprising deriving the respiration rate of the horse from the pressure variations sensed by the transducer.

9. A method of quantitatively determining the athletic condition of a horse comprising inserting a pressure sensing transducer which is connected to an electrical indicating unit into the rectal cavity of the horse, and selectively deriving the respiration rate of the horse from the pressure variations sensed by said transducer.

* * * * *